Sept. 26, 1950 J. P. REID Plant Pat. 981

PELARGONIUM PLANT

Filed June 29, 1948

INVENTOR
JOSEPH P. REID
BY C. G. Stratton
ATTORNEY

Patented Sept. 26, 1950

Plant Pat. 981

UNITED STATES PATENT OFFICE

981

PELARGONIUM PLANT

Joseph P. Reid, Huntington Park, Calif.

Application June 29, 1948, Serial No. 35,807

1 Claim. (Cl. 47—60)

Figure 1:
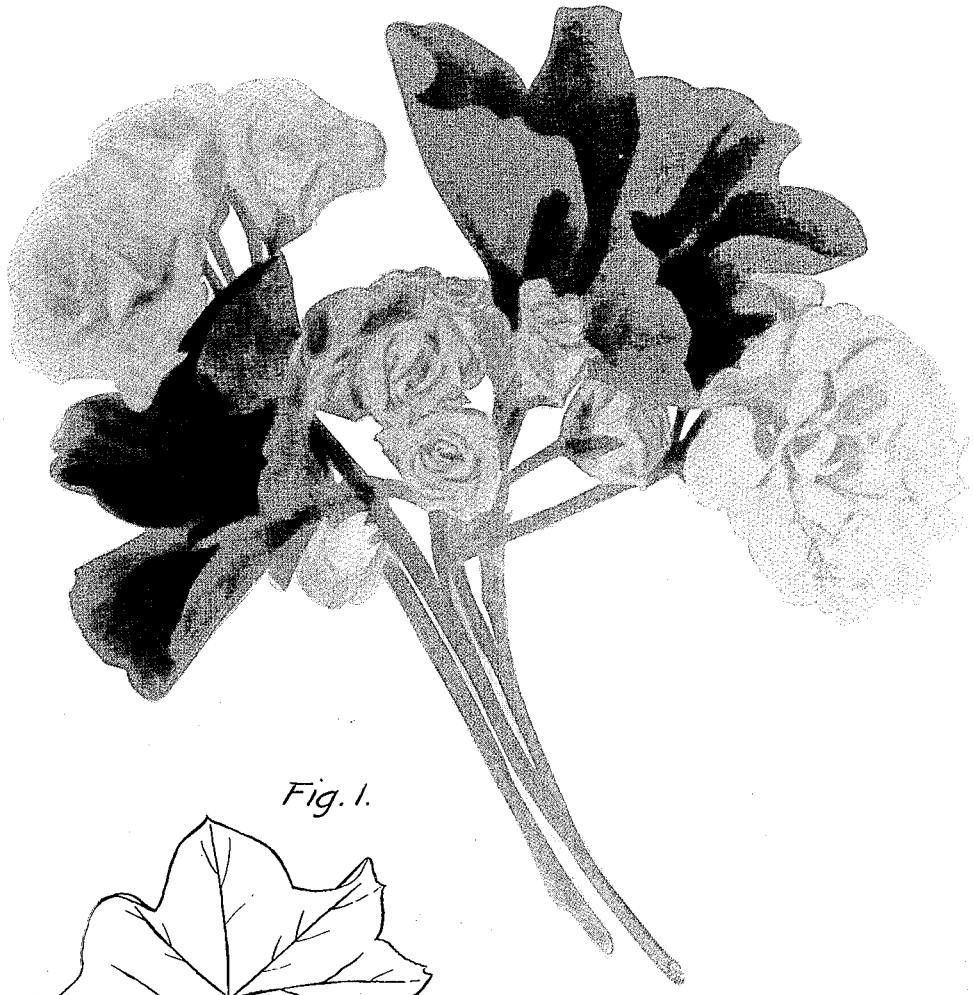
Figure 2:
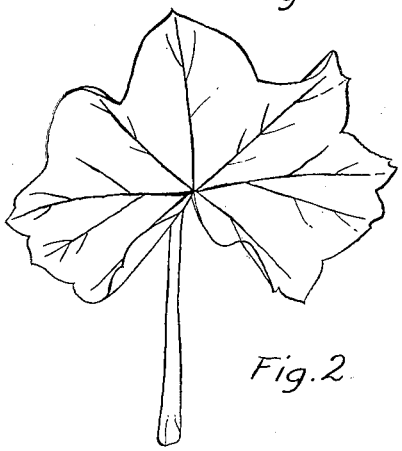

My present discovery relates to a new variety of pelargonium of the ivy geranium species, its novelty pertaining primarily to its double rose-type bud and open flower, but also including other useful improvements. The color of this new variety is rose-red. The flowers keep well when cut for decoration, often lasting seven days.

I discovered the new variety of pelargonium among a group of seedling volunteers. For several years, both on the grounds of my home and at my nursery, I asexually reproduced this new variety by tip cuttings, and the plants that I thus propagated always grew and blossomed in the true ivy geranium form, low and sprawling, and from a central root.

The new variety is an excellent plant for pot and basket culture and is a desirable plant for borders and terraces. The plant will flower in full sun or partial shade, and flowers most prolifically during the cooler months.

As the buds open, the large number of petals have substantially the same color as the fully opened blossom. The sepals of the calyx extend short of the tips of the petals and from the top, the bud appears as a full grown rose greatly resembling the Cecil Brunner rose.

As the sepals spread, their ends do not curl back but support the outer petals and as the bud blooms, the blossom retains its strong resemblance to the Cecil Brunner rose. The main color of the petals, as they increase in size, is retained particularly on the inner faces. The outer faces, however, become paler in hue from the outer edges toward the calyx, the full blown flower, as seen from the side, being shaded from a deep hue to nearly white between the sepals.

The buds, when the sepals are starting to spread, have an oval form which, as the sepals spread, have an urn form and, as the flower becomes full blown, the same have a full, high-centered form. All stages of the blossom closely resemble the similar stages of development of the Cecil Brunner rose.

The buds average approximately one-quarter inch across and the full blown flower approximates one to one and one-quarter inches across.

Following is a more detailed description of the present variety of pelargonium plant. The color names used are from Ridgeway's Color Standards and Nomenclature.

*The plant*

Growth: Bushy and luxuriant.
Disease resistance: Very high.

Blooming habit: Year around with marked prolificacy during the winter months.
Inflorescence: Roselike; small; compact center.

Foliage:

*Size.*—The average leaf is three to three and one-half inches across when the plant is pot grown. Field-grown plants have leaves that average between four and one-half to five and one-half inches in width, and two and one-half to three and one-half inches from base to tip.

*Color.*—Uniformly colored top and bottom; top, Deep Dull Yellow-Green (1) (Plate XXXI); bottom, Light Cress Green (Plate XXXI).

*Shape.*—Angle lobed; each lobe easily discerned.

*Edge.*—Alternate serrations of different depth depending on the age of the leaf; approaches three-quarters inch in mature leaf.

*Texture.*—Heavy; surface slightly rough and very shiny; the under side completely smooth except for veins.

*Stem.*—Short, heavy, smooth and obscured by foliage in potted specimens; longer in hanging basket specimens; Light Cress Green (Plate XXXI).

*Peduncle.*—Strong; very heavy; from three-quarters to one inch long; appears smooth but slightly rough to touch; Absinthe Green (Plate XXXI).

*The flower*

Bud:

*Calyx.*—Five separate sepals; sharply pointed; approximately one-half inch long; slightly rough outer surface; smooth and waxy inner surface; Absinthe Green (Plate XXXI).

*Pedicels.*—Seven-eighths to one and one-quarter inches long; very strong.

*Size.*—Slightly larger than normal.

*Color.*—Rose-Red.

*Form.*—Roselike; longer than normal ivy geranium bud.

*Opening.*—Like a rose.

Florets:

*Size.*—One to one and one-half inches across.

*Petalage.*—Tightly folded; inner petals cover reproductive organs completely; thirty-six to forty petals.

*Color.*—Rose-Red (Plate XII).

*Fragrance.*—Very mild; roselike.

*Lasting quality.*—Excellent, falls apart only when completely dried; holds color very well.

*Petals.* — Texture — delicate appearing, but durable. Shape — pear-shaped; margin clear. Size—one-half inch wide by three-quarters inch long.

Reproductive organs:

*Stamens.*—Anthers very small; develop when flower is opened by hand; filaments flat; white; short to medium length; number three to seven.

*Pistils.*—Styles, three plus; stigmas, three plus; develop when hand pollinated.

*Ovary.*—Small; smooth; light green.

The plant is most easily propagated by tip cuttings, which root readily in standard media. While hand pollinization is possible, the same is time-consuming and tedious due to the tightness of the center petals that cover the reproductive organs.

The accompanying colored drawing of the buds, blossoms and leaves of the plant, is approximately one-third larger than actual size. The outline drawing of a typical leaf is to a somewhat smaller scale.

Having thus described my invention, what I claim and desire to secure by Letters Patent is:

The new and distinct variety of pelargonium plant that is characterized by the great profusion of its Cecil Brunner roselike blossoms of rose-red color, its ivy geranium type of leaf that is relatively large as compared to the blossoms, and its low-growing, wide-spreading and prostrate form, substantially as described.

JOSEPH P. REID.

REFERENCES CITED

The following references are of record in the file of this patent:

UNITED STATES PATENTS

| Number | Name | Date |
|---|---|---|
| Pl. Pt. 424 | Sturm | Sept. 17, 1940 |